United States Patent [19]

Fuchs et al.

[11] Patent Number: 5,495,014
[45] Date of Patent: Feb. 27, 1996

[54] PREPARATION OF CAPROLACTAM

[75] Inventors: Eberhard Fuchs, Frankenthal; Tom Witzel, Ludwigshafen, both of Germany

[73] Assignee: BASF Aktiengesellschaft, Ludwigshafen, Germany

[21] Appl. No.: 358,412

[22] Filed: Dec. 19, 1994

[30] Foreign Application Priority Data

Dec. 1, 1994 [DE] Germany .......................... 44 42 727.1

[51] Int. Cl.⁶ .................................................. C07D 201/12
[52] U.S. Cl. ............................................ 540/538; 540/540
[58] Field of Search ...................... 540/538, 540

[56] References Cited

FOREIGN PATENT DOCUMENTS 3524394  1/1987  Germany ........................ 540/538

*Primary Examiner*—Robert T. Bond
*Attorney, Agent, or Firm*—Keil & Weinkauf

[57] ABSTRACT

Caprolactam is prepared by cleaving oligomers or polymers containing essentially the repeating unit —[—N(H)-(CH$_2$)$_5$—C(O)—]- in the presence of a catalyst at elevated temperatures by a process in which the cleavage is carried out in the liquid phase in the presence of a heterogeneous catalyst and of an organic solvent.

6 Claims, No Drawings

PREPARATION OF CAPROLACTAM

The present invention relates to an improved process for the preparation of caprolactam by cleaving oligomers and/or polymers containing essentially the repeating unit —[—N(H)-(CH$_2$)$_5$—C(O)—]- in the presence of a catalyst at elevated temperatures.

The cleavage of polyamide 6 (polycaprolactam) to give caprolactam is generally carried out in the presence of acidic or basic catalysts at elevated temperatures, frequently in the presence of steam at low pressure. Chem. Ing. Techn. 45 (1973) 1510 describes the technical procedure for a cleavage process with superheated steam, but a caprolactam/water solution has to be concentrated for working up.

EP-A 209 021 describes the cleavage in a fluidized alumina bed. Formation of byproducts and deactivation due to agglomeration of the catalyst bed are frequently the result. In the process according to EP 529 470, potassium carbonate is added as a catalyst for polyamide 6 cleavage, the reaction being carried out at from 250° to 320° C. with simultaneous removal of the caprolactam by distillation under reduced pressure.

The disadvantages of all processes to date for the cleavage of polyamide 6 to caprolactam are the energy-consumptive separation of large amounts of water and the removal of catalysts, such as phosphoric acids and salts thereof, potassium carbonate or alkali metal oxides.

It is an object of the present invention to provide an improved process for the preparation of caprolactam starting from oligomers and/or polymers of caprolactam, which does not have the stated disadvantages.

We have found that this object is achieved by a process for the preparation of caprolactam by cleaving oligomers or polymers containing essentially the repeating unit —[—N(H)-(CH$_2$)$_5$—C(O)—]- in the presence of a catalyst at elevated temperatures, wherein the cleavage is carried out in the liquid phase in the presence of a heterogeneous catalyst and of an organic solvent.

According to the invention, oligomers and/or polymers which contain the repeating unit —[—N(H)-(CH$_2$)$_5$—C(O)—]- are used as starting materials. Polycaprolactam and oligomers of caprolactam are preferably used, as well as copolymers of caprolactam, for example those obtained by polymerization of caprolactam in the presence of hexamethylenediamine and terephthalic acid (for example, described in EP-A 299 444).

Furthermore, it is possible to use oligomers and/or polymers of caprolactam which are to be disposed of, for example from wastes which are obtained in the preparation of caprolactam or polycaprolactam or the processing thereof to filaments, films, injection molded parts or extruded parts, and shaped articles, such as films, packaging, fabrics, filaments, fibers and extruded parts. Advantageously, the articles to be subjected to cleavage are comminuted, for example by milling, before the cleavage.

According to the invention, the reaction is carried out in the liquid phase at in general from 140° to 320° C., preferably from 160° to 300° C. The pressure is generally chosen to be from 0.5 to 25, preferably from 5 to 20, MPa, it being necessary to ensure that the reaction mixture is liquid under the conditions used. The residence times are chosen in general to be from 5 to 300, preferably from 7 to 180, minutes.

According to the invention, the cleavage is carried out without the addition of water. In a preferred embodiment, water is used, preferably from 0.5 to 20, in particular from 1 to 5, mol of water per mol of the repeating unit —[—N(H)-(CH$_2$)$_5$—C(O)—]-.

According to the invention, the cleavage is carried out in the presence of an organic solvent, the oligomers or the polymers advantageously being used in the form of a 1–50, in particular 5–40, particularly preferably 5–25, % strength by weight solution in the organic solvent, a mixture of water and the organic solvent with the abovementioned percentages by weight of the oligomers and/or polymers particularly preferably being used.

Examples of organic solvents are $C_1$–$C_{10}$-alkanols, such as methanol, ethanol, n-propanol, isopropanol, n-butanol, isobutanol, sec-butanol, n-pentanol, n-hexanol, n-heptanol, n-octanol, n-nonanol and n-decanol, in particular $C_1$–$C_4$-alkanols, such as methanol, ethanol, n-propanol, isopropanol, n-butanol, isobutanol and sec-butanol, particularly preferably methanol, ethanol, n-propanol and n-butanol;
polyols, such as diethylene glycol and tetraethylene glycol, preferably tetraethylene glycol;
hydrocarbons, such as petroleum ether, benzene, toluene and xylenes;
lactams, such as pyrrolidone and caprolactam, and substituted N—$C_1$–$C_4$-alkyllactams, such as N-methylcaprolactam, N-ethylcaprolactam and N-methylpyrrolidone.

In a further embodiment from 0 to 5, preferably from 0.1 to 2, % by weight of ammonia and/or hydrogen and/or nitrogen may be added to the reaction mixture.

The heterogeneous catalysts used may be, for example: acidic, basic or amphoteric oxides of the elements of the second, third or fourth main group, such as calcium oxide, magnesium oxide, boron oxide, alumina, tin oxide or silica as pyrogenic silica, silica gel, kieselguhr, quartz or mixtures thereof, and oxides of metals of the second to sixth subgroups of the Periodic Table such as titanium oxide, in amorphous form or as anatase or rutile, zirconium oxide, zinc oxide, manganese oxide or mixtures thereof. For example, oxides of lanthanides and actinides, such as cerium oxide, thorium oxide, praseodymium oxide, samarium oxide, neodymium oxide, rare earth mixed oxides and mixtures thereof with the abovementioned oxides may also be used. Further catalysts may be, for example: vanadium oxide, niobium oxide, iron oxide, chromium oxide, molybdenum oxide, tungsten oxide and mixtures thereof. Mixtures of these oxides with those of second, third and fourth main groups are also possible. Some sulfides, selenides and tellurides such as zinc telluride, zinc selenide, molybdenum sulfide, tungsten sulfide and sulfides of nickel, of zinc and of chromium, may also be employed.

The abovementioned compounds may be doped with compounds of main groups 1 and 7 of the Periodic Table or may contain these.

Further catalysts are, for example, zeolites, phosphates and heteropoly acids and acidic and alkaline ion exchangers, such as Naphion®.

If required, these catalysts may contain up to 50% by weight in each case of copper, tin, zinc, manganese, iron, cobalt, nickel, ruthenium, palladium, platinum, silver or rhodium.

Depending on the composition of the catalyst, the latter may be used as an unsupported or supported catalyst. For example, titanium dioxide may be used as titanium dioxide extrudates or as titanium dioxide applied in a thin layer on a carrier. Observations to date have shown that all methods described in the literature can be used for applying titanium dioxide to a carrier such as silica, alumina or zirconium dioxide. Thus, a thin titanium dioxide layer can be applied by hydrolysis of titanium organyls, such as titanium isopropylate or titanium butylate, or by hydrolysis of titanium tetrachloride or other inorganic titanium-containing compounds. Sols containing titanium oxide may also be used.

The advantage of the novel process is that, in contrast to prior art processes, very energy-consumptive separation of large amounts of water and the removal of catalysts, such as phosphoric acids and salts thereof, potassium carbonate or alkali metal oxides, are dispensed with.

EXAMPLES

EXAMPLE 1

A 10% strength by weight solution of 6-aminocapronitrile (ACN) in 6.4% by weight of water and 83.6% by weight of ethanol was passed, at 200° C. and 100 bar, into a heated tube reactor having a capacity of 25 ml, a diameter of 6 mm and a length of 800 mm and filled with titanium dioxide (anatase) in the form of 1.5 mm extrudates. The residence time was 30 minutes. The product stream leaving the reactor was analyzed by gas chromatography and high-pressure liquid chromatography. Conversion to caprolactam: 100%, selectivity with respect to caprolactam: 88%.

The mixture thus obtained was subjected to a distillation (temperature: 110° C., pressure: 0.1 mbar) to obtain caprolactam, a mixture consisting of 9% by weight of oligomers and polymers, 1% by weight of caprolactam, 6.4% by weight of water and 83.4% by weight of ethanol remaining as the bottom product.

EXAMPLE 2

(a) 60 ml/h of the bottom product from Example 1 were fed at 100 bar into a tube reactor heated to 230° C., having a capacity of 25 ml, a diameter of 6 mm and a length of 800 mm and filled with titanium oxide (anatase) in the form of 1.5 mm extrudates. The residence time in the reactor was 15 minutes.

The conversion to caprolactam was 53%, based on the amount of oligomers and polymers used which had the repeating unit —[—N(H)-(CH$_2$)$_5$—C(O)—]-.

EXAMPLES 3, 4, AND 5

Example 2 was repeated with the differences shown in the table below.

TABLE

| Example | Temperature [°C.] | Residence time [min] | Conversion [%] |
|---------|-------------------|----------------------|----------------|
| 3 | 220 | 15 | 50 |
| 4 | 220 | 30 | 62 |
| 5 | 250 | 10 | 63 |

We claim:

1. A process for the preparation of caprolactam by cleaving oligomers or polymers containing essentially the repeating unit —[—N(H)-(CH$_2$)$_5$—C(O)—]- in the presence of a catalyst at elevated temperatures, wherein the cleavage is carried out in the liquid phase in the presence of a heterogeneous catalyst and of an organic solvent.

2. A process as claimed in claim 1, wherein the reaction is carried out at from 140° to 320° C.

3. A process as claimed in claim 1 or 2, wherein the reaction is carried out at a concentration of the oligomers or polymers of from 5 to 50% by weight.

4. A process as claimed in any of claims 1 to 3, wherein the residence time is chosen to be from 5 to 300 minutes.

5. A process as claimed in any of claims 1 to 4, wherein the organic solvent used is a C$_1$–C$_4$-alkanol or tetraethylene glycol.

6. A process as claimed in any of claims 1 to 5, wherein the cleavage is carried out in the presence of water.

* * * * *